United States Patent
Tjepkes et al.

(10) Patent No.: US 12,062,273 B2
(45) Date of Patent: Aug. 13, 2024

(54) FAUCET FOR HANDWASHING FEEDBACK WITH INTEGRATED DISPENSER

(71) Applicant: Abluo, Inc., Mound, MN (US)

(72) Inventors: Joel Roger Tjepkes, Mound, MN (US); Gene O'Brien, Mound, MN (US)

(73) Assignee: Abluo, Inc., Mound, MN (US)

( * ) Notice: Subject to any disclaimer, the term of this patent is extended or adjusted under 35 U.S.C. 154(b) by 274 days.

(21) Appl. No.: 17/384,494

(22) Filed: Jul. 23, 2021

(65) Prior Publication Data
US 2022/0028247 A1    Jan. 27, 2022

Related U.S. Application Data

(60) Provisional application No. 63/055,878, filed on Jul. 23, 2020.

(51) Int. Cl.
| | | |
|---|---|---|
| G08B 21/24 | (2006.01) | |
| A47K 5/12 | (2006.01) | |
| A61L 2/00 | (2006.01) | |
| A61L 2/28 | (2006.01) | |
| G09B 19/00 | (2006.01) | |

(52) U.S. Cl.
CPC .......... *G08B 21/245* (2013.01); *A47K 5/1202* (2013.01); *A47K 5/1217* (2013.01); *A61L 2/0088* (2013.01); *A61L 2/28* (2013.01); *G09B 19/0076* (2013.01); *A61L 2202/14* (2013.01); *A61L 2202/17* (2013.01)

(58) Field of Classification Search
CPC .. G08B 21/245; A47K 5/1202; A47K 5/1217; A61L 2/0088; A61L 2/28; A61L 2202/14; A61L 2202/17; A61L 2202/15; A61L 2/0047; A61L 2/24; G09B 19/0076
See application file for complete search history.

(56) References Cited

U.S. PATENT DOCUMENTS

| | | | |
|---|---|---|---|
| 6,038,331 A * | 3/2000 | Johnson | G08B 21/00 382/173 |
| 10,121,149 B2 | 11/2018 | Davis et al. | |
| 2010/0326472 A1 | 12/2010 | Glenn et al. | |
| 2015/0199883 A1 | 7/2015 | Hartley et al. | |
| 2016/0296077 A1 * | 10/2016 | Smith | A61L 2/0047 |
| 2018/0160863 A1 * | 6/2018 | Xu | A47K 5/00 |
| 2021/0312788 A1 * | 10/2021 | Paliath-Pathiyal | G08B 21/245 |
| 2021/0366265 A1 * | 11/2021 | Lazzi | G08B 21/245 |
| 2021/0369881 A1 * | 12/2021 | Hayden | A61L 2/0023 |
| 2021/0388585 A1 * | 12/2021 | Hamilton | E03C 1/057 |
| 2022/0008593 A1 * | 1/2022 | Smith | A61L 2/0088 |

(Continued)

*Primary Examiner* — An T Nguyen
(74) *Attorney, Agent, or Firm* — David J. McKinley; Larkin Hoffman Daly & Lindgren, Ltd.

(57) ABSTRACT

A "smart-faucet" is provided that provides instructions and feedback to a user that improves the efficacy of a handwashing event. The faucet includes a supply of sanitizer that includes a visualization component, such as a fluorescent component, that assists the user in determining sanitizing coverage of the hands. The visualization component may require the presence of an energy source radiating a specific frequency, such as UV, in order to become visible. The faucet may further be able to communicate information to a remote location regarding supply data necessary to insure just in time delivery of a replacement supply of sanitizer.

13 Claims, 4 Drawing Sheets

(56) References Cited

U.S. PATENT DOCUMENTS

2022/0157152 A1* 5/2022 Broyden .................. G07C 3/00
2023/0270904 A1* 8/2023 Simonovsky ............. A61L 2/24
                                                          4/668

* cited by examiner

FAUCET FOR HANDWASHING FEEDBACK WITH INTEGRATED DISPENSER

RELATED APPLICATIONS

This application claims priority to U.S. Provisional Application Ser. No. 63/055878 filed Jul. 23, 2020 entitled UV Light Sink Faucet, which is hereby incorporated herein by reference in its entirety.

FIELD OF THE INVENTION

The field of the invention relates generally to devices and methods for improving hand cleanliness by providing feedback and guidance during the handwashing process.

BACKGROUND OF THE INVENTION

The importance of proper handwashing is irrefutable and has never been so apparent as it has become in recent history. A challenge with handwashing has always been feedback. Germs are invisible. People may be unaware that they are unsuccessful with washing hands because they have no tool to see results of proper cleansing agent application and lathering. Additionally, cleansing agents are effective because they are surfactants. They break down the hydrophobic surface tension barrier of oils and allow the water used in conjunction with the cleansing agent to penetrate oils on the skin, which tend to attract and trap pathogens, and mechanically wash them away. The surfactant quality of cleansing agent further destroys the bacterial capsule, killing the bacteria. However, these effects of cleansing agent are enhanced by scrubbing and take time, typically 20-30 seconds, and are only effective where the cleansing agent is present. It is not uncommon for people using cleansing agent and water to rinse the cleansing agent off long before the cleansing agent has accomplished these desired sanitizing effects.

There have been many attempts to improve handwashing over simple cleansing agent and water techniques. For example, alcohol-based hand sanitizers have become widely popular due to their ease of use and perceived effectiveness. However, though hand sanitizer may be effective at destroying certain pathogens on contact, the user has no way of being confident that all the surfaces of the hands have been sanitized. Hand sanitizers are also less effective at mechanically removing dirt and other contaminants from hands as they are used without a rinsing step. Additionally, most alcohol-based hand sanitizers are flammable and tend to dry or otherwise damage skin when used frequently.

Other attempts at providing a more advanced solution to ensuring effective handwashing are shown and described in U.S. Pat. No. 10,121,149; 2010/0326472A1; and 2015/0199883, all of which are incorporated by reference herein in their entireties.

There is thus a need for an effective handwashing device and method that addresses the aforementioned shortcomings by providing guidance and feedback to ensure a user thoroughly cleans the surfaces of the hands. There is a further need for such a device and method to accomplish these goals in a manner that is quick and convenient, and also engaging enough to capture the users attention, thereby encouraging the user to complete the process.

OBJECTS AND SUMMARY OF THE INVENTION

The various embodiments of the invention described herein addresses these needs by providing a handwashing apparatus and method that provides feedback to the user as to whether their hands have been washed effectively. More specifically, the various embodiments of the invention are directed to an automated or semi-automated handwashing system that engages and guides the user through the handwashing process by providing visual and/or auditory feedback on the effectiveness of the handwashing attempt to the user, and preferably including a handwashing-effectiveness, data-gathering feature that the system uses as input for determining what information to convey to the user, as well as a determinator for advancing to the next step in the process.

In one embodiment the system includes a sanitizing solution having a visual component allowing the user to view coverage.

In another embodiment the system includes a sanitizing solution having a visual component that further allows the system to analyze coverage.

In another embodiment the system includes a visualization activating mechanism that illuminates the sanitizing solution to provide the user feedback.

In still another embodiment the sanitizing solution is only visible in the presence of a visualization activating mechanism.

One embodiment of the visualization activating mechanism is visible light, UV light, or infra red light.

In another embodiment the visualization activating mechanism is mixing of chemical components.

Another embodiment provides a lighted fixture assembly for cleaning a user's hands that has a faucet assembly for drawing or regulating the flow of water through at least one pipe assembly disposed therein, a proximal end of the at least one pipe assembly coupled to a water supply, the pipe assembly leading to an outlet at a distal end of the at least one pipe assembly.

In at least some embodiments, one or more light assemblies are disposed substantially on an underside surface of the faucet assembly and is designed to shine downwardly on the user's hands. At least one secondary pipe assembly is disposed within an interior portion of the faucet assembly, a proximal end of the at least one secondary pipe assembly coupled to a supply of a cleansing agent and/or a visualization component, an open distal end of the at least one secondary pipe assembly substantially adjacent to the distal end of the at least one pipe assembly and designed to dispose one or both of the cleansing agent and/or the visualization component.

A user interface assembly may be provided on an upper surface of the faucet assembly designed to display cleaning instructions for cleaning the user's hands. Alternatively, the display may be mounted remotely from the faucet assembly.

At least one sensor assembly may be disposed substantially on the underside of the faucet assembly and substantially adjacent to the at least one light assembly, the at least one sensor assembly designed to sense the presence of the user's hands beneath the distal end of the at least one pipe assembly.

A control unit may be disposed within or outside of the faucet assembly, the control unit communicatively coupled to the screen assembly and the sensor assembly and designed to control the screen assembly and a valve assembly disposed within or outside of the faucet assembly for regulating the flow of water through the at least one pipe assembly. At least one power supply assembly is provided to power the lighted fixture assembly.

In one embodiment of the lighted fixture assembly for cleaning a user's hands, a removable cleansing agent container and a removable visualization component container are coupled to the faucet assembly and designed to be filled with a cleansing agent or visualization component therein.

In one embodiment of the lighted fixture assembly for cleaning a user's hands, the screen assembly consecutively displays instructions, graphical or written or both, that the user should position hands under the sensors to start the wash, that the faucet assembly is dispensing cleansing agent and visualization component, that the user should begin applying the cleansing agent and visualization component, that a programmable timer, for example a twenty-second countdown, is underway for cleansing with the cleansing agent, that the user should begin rinsing, and that the wash is complete.

The control requirements, and so controller functionality and apparatus, depend strongly on the capabilities of a particular embodiment. Control approaches include, but are not limited to: some simple embodiments could be implemented with mechanical or electrical timers; embodiments with graphical user interfaces could benefit from control via a local micro-computer; embodiments with data-reporting capability could benefit from a local micro-computer with data storage, or connection to a remote server or to the "cloud" to store the data; or embodiments that have the control function reside remotely, such as in a server or the cloud.

A proximity sensor, optical sensor or motion detector is an electrical device that utilizes a sensor to detect nearby motion or proximity. Such a device is often integrated as a component of a system that automatically performs a task or alerts a system of motion or presence in an area.

One aspect of the invention provides the ability for users to see how well they are washing their hands with programmable instructions and timed intervals for lathering and rinsing.

Another aspect of the invention provides a device that informs a user when they have ineffectively washed their hands.

In one embodiment of the inventive concept, a single water faucet has a built-in sensor, a cleansing agent dispenser built in, a visualization component dispenser built in, a light built in, a screen display to step the user through the washing process, including programmable instructions and timed intervals for lathering and rinsing.

In one embodiment of the inventive concept, the user has the option to turn operating elements off. Users may choose not to dispense visualization components and just use the faucet as a dual cleansing agent and water fixture. Users may choose to use or forgo the screen displays. Users may choose to adjust the timed intervals of the screen displays. Users may choose to forgo the light.

Single faucet fixtures with built-in sensors that provides cleansing agent and visualization component dispensing may have a screen display to guide users through the process with timed intervals and a light to aid in proper application of cleansing agent, providing feedback on hand washing performance.

The visualization components of the sanitizing solution comprise dyes, fluorescent components, phosphorescent components, or chemiluminescent components. Examples of dyes include, but are not limited to indigo, FD&C red 40, ferrous lactate, turmeric, and fruit juices. Some dyes are also fluorescent components, phosphorescent components, or chemiluminescent components. Examples fluorescent components include, but are not limited to fluorescein, rhodamine, riboflavin, and fluorescent proteins. Some fluorescent components are also dyes, phosphorescent components, or chemiluminescent components. Examples of phosphorescent components include, but are not limited to luminescent zinc sulfide and activated strontium aluminate. Some phosphorescent components are also dyes, fluorescent components, or chemiluminescent components. Chemiluminescent components require mixing with another component to activate visualization. Examples of chemiluminescent mixtures include but are not limited to luminol mixed with hydrogen peroxide, lophine mixed with air and sodium hydroxide. Some chemiluminescent components are also dyes, fluorescent components, or phosphorescent components. Chemiluminescent systems can contain a catalyst to promote the generation of light. Forms that the visualization component can take include, but are not limited to: added liquids or dissolved substances that act as visualization components; solids, often in the form of flakes, needles or powders, that are themselves visualization components; solids, often in the form of flakes, needles or powders, that act as inactive or active carriers for visualization components; active carriers that are treated with other visualization components to alter their optical properties; and mixtures of the above active and inactive components.

It would be advantageous to have a lighted fixture assembly that shines light onto a user's hands and reacts with a visualization component. Furthermore, it would be advantageous to have an apparatus that is reusable. Still further, it would be advantageous to have a lighted fixture assembly that is digital and/or activated by a controller.

The inventive concept advantageously fills the aforementioned deficiencies by providing a reactive cleansing agent that reacts to a lighted faucet assembly, which provides a way to effectively wash and clean hands.

The lighted faucet assembly may have a digital display screen.

The lighted faucet assembly may have a UV, visible, or infrared light.

The lighted faucet assembly fulfills the need for a sanitary sink faucet.

Among other things, it is an advantage of the inventive concept to provide a lighted faucet assembly that does not suffer problems or deficiencies associated with prior solutions.

It is still further an advantage of the lighted faucet assembly to have refillable components.

Still further, the lighted faucet assembly may have a timer.

In one embodiment, a handwashing apparatus is provided that includes a housing; a water line having an open end and a connected end, the connected end being connectable to a water supply, the open distal end terminating at a user end of the housing to provide water to a user; a sanitizer line having a distal end and a proximal end, the proximal end connectable to a sanitizer reservoir and the distal end terminating adjacent the open end of the water line; sanitizing solution contained within the sanitizer line, the sanitizing solution including a visualization component and a base component, the visualization component providing visual feedback to a user under a predetermined lighting environment; a pump in operable association with the sanitizer reservoir; a controller; a sensor mounted on the housing and capable of sending a signal to the controller when a user's hand comes within an operable proximity of the sensor; and a user interface that communicates instructions to a user during a handwashing sequence.

This handwashing apparatus may also include a camera mounted on the housing and in data communication with the controller, a server, or the cloud.

The handwashing apparatus may also include a camera remotely mounted and in data communication with the controller, a server, or the cloud.

The visualization component may be a dye. In this case the predetermined lighting environment would be ambient light and/or a visible light source.

Alternatively, the visualization component may be an additive that becomes visible only in the presence of a predetermined energy source. The predetermined energy source may be UV, visible, or infrared light. Furthermore, the light source may be mounted to the housing.

One embodiment of the invention is a method of washing hands including the following steps: providing a handwashing apparatus including a sequence and a user interface; beginning a handwashing event by placing hands under the handwashing apparatus, thereby automatically initiating the sequence; providing instruction via the user interface to keep the hands in engagement with the handwashing apparatus until water and a sanitizing solution is dispensed; changing an optical property of the sanitizing solution by activating an energy source onto the sanitizing solution present on the hands; instructing the user to ensure that all surfaces of the hands are to be covered with the sanitizing solution; dispensing water when a predetermined criteria is met and instructing the user via the user interface to rinse the hands until the sanitizing solution is gone.

This method may optionally include recording usage data associated with the handwashing event. This usage data could be used to determine an amount of sanitizing solution remaining in a supply reservoir. The usage data may also provide statistics to an employer, such as compliance handwashing data. The usage data may also be sent to a government agency, such as the Center for Disease Control (CDC) for research purposes.

The step of providing instruction via the user interface may be accomplished by providing visual and/or audio instruction via the user interface.

The step of activating an energy source may be executed by activating a light source, such as a UV, infrared, deep blue, black or visible light source.

The step of changing an optical property may be executed by mixing chemical components.

The step of dispensing water when a predetermined criteria is met may include dispensing water after a predetermined time interval has elapsed.

The method of handwashing may include using a camera connected to the handwashing apparatus to automatically determine whether the surfaces of the hands are sufficiently covered and/or scrubbed with the sanitizing solution. If so, then the step of dispensing water when the predetermined criteria is met may include dispensing water when the handwashing apparatus has determined the surfaces of the hands are sufficiently covered and/or scrubbed with the sanitizing solution using the camera.

One embodiment of the invention provides a handwashing apparatus that includes: a dispensing apparatus that uses a sensor to determine the presence of a user's hands; a supply of water dispensable by the handwashing apparatus; a supply of sanitizing solution dispensable by the handwashing apparatus; a controller associated with the handwashing apparatus that executes the handwashing sequence upon receiving a signal from the sensor.

The sequence may include: a water dispensing step; a sanitizing solution dispensing step; a handwashing assistance step; and a rinsing step.

The handwashing assistance step may include providing visualization assistance to the user that helps the user determine thorough coverage of the hands with the sanitizing solution; and wherein the rinsing step is not activated until a criteria has been met.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1:
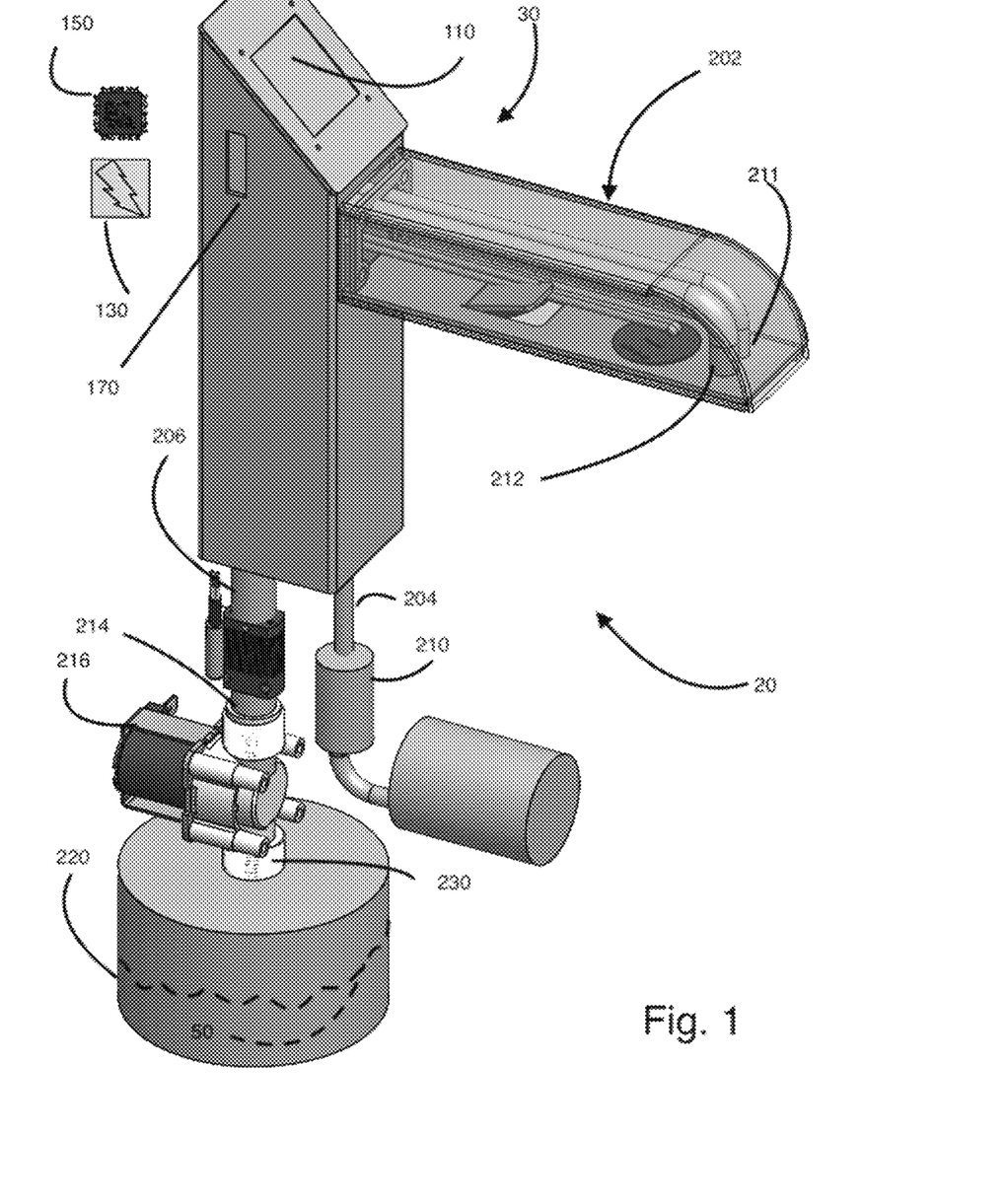
FIG. 1 is a perspective view of an embodiment of the invention.

Referring first to FIG. 1 there is a diagram showing the various faucet components of at least one embodiment of the invention. One skilled in the art will understand that any of the embodiments of the various components may be configured in combination with the embodiments of the other components in innumerable combinations.

FIG. 1 is a diagrammatic view that shows a handwashing apparatus 20 that generally includes a dispensing apparatus 30, a sanitizing solution 50, a visualization activating mechanism 70 (FIG. 6), an automatic monitoring system 90 (FIG. 6), a user interface 110, a power supply 130, a controlling mechanism 150, and a communications modality 170. The various embodiments of each of these components will be discussed separately.

Dispensing Apparatus

FIGS. 1-7 show various components of an embodiment 20 of a dispensing apparatus 30 that generally includes a housing 202 in the form of a faucet that contains a water line 204 and a sanitizer line 206. The water line 204 is connected to a water source, which may be a conventional water supply line or may be an independent water reservoir. Conventional water supplies provide water pressure created by elevated water towers that get refilled via pumps when a lower limit is reached. If the water line 204 is not plumbed to a conventional water supply line in favor of an independent water reservoir, water pressure may be provided by elevating the water reservoir above the level of the faucet housing 202, or by providing a powered pump, or by a pressurized storage vessel.

In one embodiment, the water line 204 is connects to the water supply via an electronically controlled valve 210, such as a solenoid or other type of valve, that opens and closes according to commands from either the controlling mechanism 150 and/or the automatic monitoring system 90, thus allowing the system to automatically turn the water on and off according to the logic sequences described in detail below.

In another embodiment, each dispensing apparatus further includes an in-line electric heater (not shown) associated with the water source or water line 204. This heater may be controlled by the controlling mechanism 150 such that the desired heat may be set by a user or technician using the user interface 110 or an alternative programming modality like a smart phone or a proprietary handheld device, or even using a computer from a remote location. In at least one embodiment, the handwashing apparatus 20 includes a user identification capability that identifies the user. In these embodiments, the user may set a personal desired water temperature for the handwashing apparatus 20, or for a network of handwashing apparatuses such that any handwashing apparatus 20 in the network will be able to identify the user and set the heater to the desired temperature while the identified user is using the faucet. Limits may additionally be set such that a minimum effective temperature is used and a maximum safe temperature is not exceeded.

The sanitizer line 206 has a distal end 212 and a proximal end 214. The distal end 212 is a terminus that is adjacent to the outlet 211 of the water line 204. This location is preferably under the housing, similar to the water outlet of a conventional faucet. The proximity of the distal end 212 of the sanitizer line 206 to the water outlet 211 allows a user to receive both water and sanitizing solution 50 without having to remove their hands from under the housing 202.

The proximal end 214 of the sanitizer line 206 is connected to a sanitizer reservoir 220, either directly or via a pump 216. In one embodiment the pump 216 is a peristaltic pump that connects around an outside surface of the sanitizer line 206. Peristaltic pumps can be advantageous as they do not come in contact with the liquid being delivered through the line. In another embodiment, the sanitizer reservoir 220 is an easily compressible, disposable bladder, and the pump 216 is a compressing mechanism that surrounds and squeezes the reservoir 220 in order to dispense the sanitizing solution. Other pump configurations may also be used as are known in the art of liquid dispensation. The pump 216 is activated by the controlling mechanism 150 such that the sanitizing solution is dispensed according to the logic sequences described in detail below.

Figure 2:
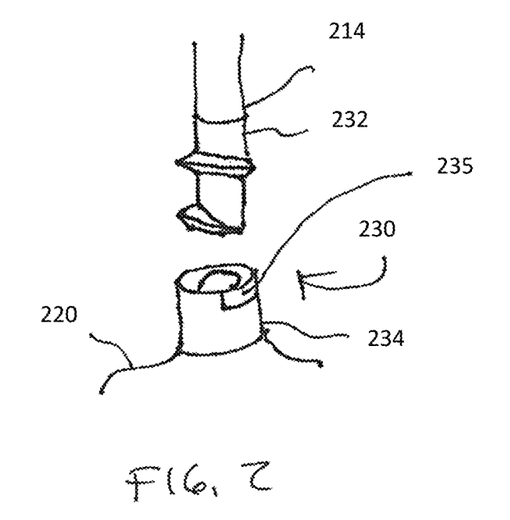
FIG. 2 is a perspective view of an embodiment of a connector used in the present invention.
Figure 3:
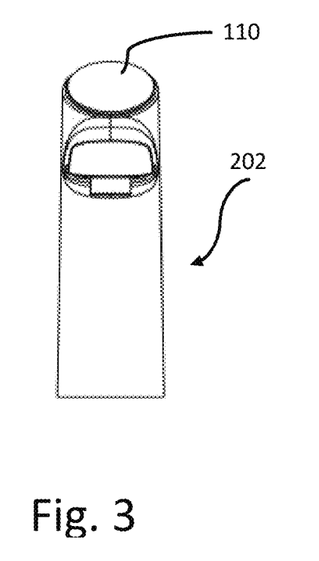
FIG. 3 is a front elevation of an embodiment of a housing of the invention.
Figure 4:
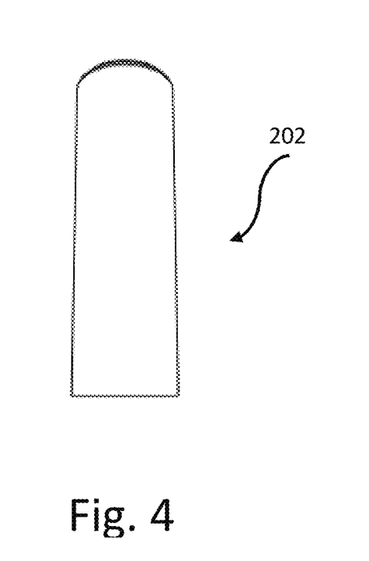
FIG. 4 is a rear elevation of an embodiment of a housing of the invention.
Figure 5:
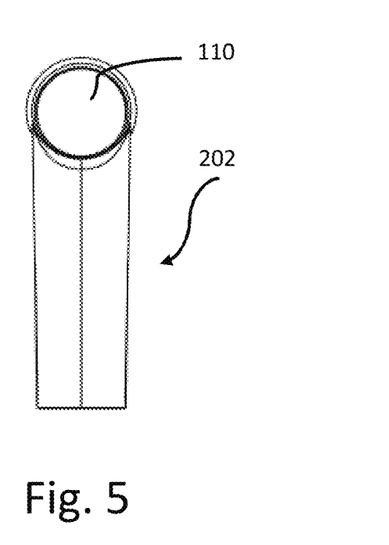
FIG. 5 is a top plan view of a housing an embodiment of the invention.

The sanitizer reservoir 220 may be provided in the form of a rigid container or in the form of a bladder as described above. FIG. 2 shows a connector 230 that includes a first component 232 and a second component 234 that are provided in order to make the connection between the proximal end 214 of the sanitizer line 206 and the reservoir 220. The connector 230, in some embodiments is in the form of a simple luer lock, or similar connectors known in the art, or may include a proprietary configuration that the sanitizer is received from a predetermined, approved source.

In other embodiments, additional or alternative measures may be utilized to ensure that only approved sanitizers are used with the dispensing apparatus 30. For example, in some embodiments, an RFID chip 235 is incorporated into the second component 234 that provides a verification signal to the controlling mechanism 150 indicating the approved sanitizer source. In other embodiments, the sanitizer reservoirs 220 include a scannable code on an outside surface thereof that is readable by one of the components of the dispensing apparatus, such as a component of the automatic monitoring system 90. If it is determined that an unacceptable sanitizing solution is being used, the controller may take appropriate actions such as disabling the pump or sending an alert to the manufacturer and voiding the warranty.

The housing 202 also serves as a mounting platform for the visualization activating mechanism 70, the automatic monitoring system 90 and the user interface 110. In some embodiments, the housing 202 may also serve as a mounting platform for the power supply 130, and/or the controller mechanism 150, and/or the communications modality 170.

In at least one embodiment, the housing 202 is removably attached to a fixed structure such as a sink or countertop. Removal of the housing 202, such as in the case of repairs or warranty replacement, is accomplished by removing the connectors between the housing and the fixed structure. The water line 204 and sanitizer line 206 are preferably flexible and long enough to allow the detached housing to be lifted from the countertop, pulling the lines 204 and 206 above the countertop to allow access to quick release couplings present in the lines 204 and 206, as well as an electrical connection to the power supply 130.

Sanitizing Solution

The sanitizing solution 50 used with the handwashing apparatus 20 generally includes a liquid cleansing agent base mixed with a visual component. The visual component, in one embodiment, may be in the form of a UV or near UV activated additive that remains invisible unless illuminated by UV or near UV light. This embodiment prevents discoloration of the sink and countertops. In other embodiments of the sanitizing solution 50, the visual component is activated by other wavelengths of light. For example, the visual component may be activated by visible light, infrared light or by black light (UV-A). In still other embodiments, the visual component comprises two chemical that, when mixed together, react and forms a glowing solution that does not need an external light source to visualize.

Compounds that glow under light comprise dyes, fluorescent components, and phosphorescent components, and chemiluminescent components.

One example of a sanitizing solution usable with the handwashing apparatus includes a liquid cleansing agent base mixed with Fluorescein at a ratio of 0.01 wt %.

In some embodiments, the sanitizing solution 50 generally includes a liquid cleansing agent base mixed with a visualization component that helps the user visualize areas on the hand which the user has neglected to cover with the sanitizing solution 50. The visualization component may have one or more of the following qualities: a coloration that disappears over time such that sinks and countertops appear clean after use; an attractant that causes the visualization component to cling to dirt or oil such that after rinsing, any unclean areas of the hands remain discolored with the visualization component; a visualization quality that makes the visualization component easily readable by an optical scanner.

In at least one embodiment, the sanitizing solution includes a visualization component that gets activated when mixed with another solution. This embodiment includes two containers that each have a line extending through the housing. The two liquids would then mix on the user's hands during the washing procedure, or a mixing chamber may be provided.

In at least one embodiment, the visual component comprises a reflective suspension that reflects light from a light source, making visualization easier for the user.

Visualization Activating Mechanism

The visualization activating mechanism 70 is selected to be compatible with the visual component of the sanitizing solution 50. For example, if the visual component is activated by deep blue light, the visualization activating mechanism 70 is a deep blue light source. If the visual component is activated by UV-A light, the visualization activating mechanism 70 is a UV-A "black light" source.

In the event that a visual dye is used as the visual component, the visualization activating mechanism 70 may be unnecessary, or may be a white light source or a specific-colored light source chosen to maximize the contrast of the visual component with the skin, either for the user, the automatic monitoring system 90, or both.

Automatic Monitoring System

Figure 6:
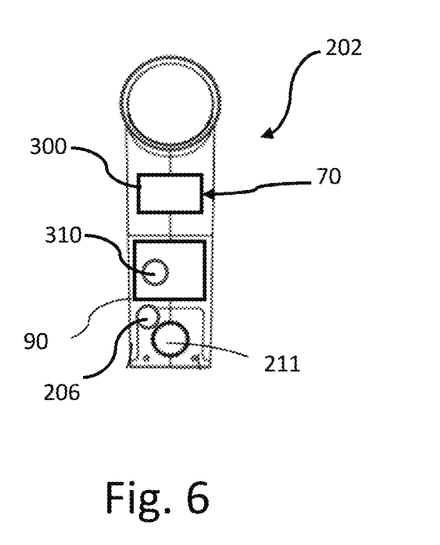
FIG. 6 is a bottom plan view of a housing an embodiment of the invention.

As shown in FIG. 6, the automatic monitoring system 90 generally includes one or more sensors located on a bottom surface or recess of the housing 202, or on a vertical surface or recess of the housing 202, such that the one or more sensors are directed at the hands of the user. In at least one embodiment, the automatic monitoring system 90 includes an proximity or other sensor 300 that can detect the presence of hands placed in proximity to the proximity sensor 300.

In at least one embodiment, the proximity sensor 300 is used in conjunction with a camera or scanner 310 that is capable to analyzing the presence and/or coverage of the sanitizing solution on the user's hands. Alternatively, the proximity sensor 300 has the additional capabilities of serving as the camera or scanner 310, obviating the need for two components.

In at least one embodiment, the proximity sensor 300, and/or camera or scanner 310, further includes the capability of reading a barcode or QR code to verify the authenticity of the sanitizing solution 50. As discussed above, the proximity sensor 300, and/or camera or scanner 310 may have a user identification feature. In one embodiment, the user identification feature is a fingerprint identification capability, which may also be associated with the user interface 110. In another embodiment, the user identification may be in the form of a face identification ability associated with the user interface 110, which necessarily faces the user, and is discussed in more detail below. In another embodiment, user identification can involve detecting an identification device such as an ID badge, either thru optical means by the sensor 300 or the scanner 310, or by RFID, or other modalities. In still other embodiments, especially in the context of users that are held to compliance standards, each user may be issued an identification device such as a ring that includes a Bluetooth signature, a scannable code, a magnetic signature, or the like, that is worn continually and communicates with the handwashing apparatus 20.

In at least one embodiment, the camera 310 has a record feature that records video of the handwashing being performed. This video is temporarily stored on the controller 150, a local server, or a cloud-based server. The video may be used to provide feedback to the user in order to improve their handwashing technique, or it may be stored for longer durations to be used as evidence of non-compliance in a professional setting.

Controller

The control requirements, and so controller functionality and apparatus, depend strongly on the capabilities of a particular embodiment. Control approaches include, but are not limited to: some simple embodiments could be implemented with mechanical or electrical timers; embodiments with graphical user interfaces could benefit from control via a local micro-computer; embodiments with data-reporting capability could benefit from a local micro-computer with data storage, or connection to a remote server or to the "cloud" to store the data; it would even be possible to have the control function reside remotely, such as in a server or the cloud.

The controller 150 controls the various components of the handwashing apparatus 20 and executes a logic sequence when a user triggers the automatic monitoring system 90. The controller also provides commands to the user interface 110.

In at least one embodiment, the controller 150 controls both the visual and audio components of the user interface 110. The controller 150 further has a timing function such that minimum time intervals may be set for the various steps in the washing method. For example, in one embodiment, there is an initial wetting step followed by a cleansing agent dispensing step. The cleansing agent dispensing step is followed by a scrubbing interval in which the user is to scrub their hands. Rinse water is not dispensed until a predetermined time interval has elapsed. Thus, the controller 150 may use the timing function as one input criteria for advancing the sequence.

In at least one embodiment, the controller 150 controls the water flow through the water line 204. This may be accomplished by electrically controlling the solenoid valve 210. For example, as explained above, the controller may use the solenoid valve to start and stop the water based on predetermined sequences and/or criteria being met. If a pump is being used to create water flow from an independent reservoir, the pump may be controlled by the controller in a similar fashion.

In at least one embodiment, the controller 150 controls the pump 216 that creates flow through the sanitizer line. The pump 216 may be controlled by a set on/off sequence that dispenses a metered amount of sanitizer for each washing. By setting a known, metered amount of dispensed sanitizer, an accurate reservoir level may be tracked, allowing automatic refill ordering to take place.

In at least one embodiment, the controller 150 may use this metric to monitor not only a usage amount, but also to calculate a usage rate. The usage rate may be used to predict when a replacement reservoir is needed. The controller may further note the time of the reorder issuance in comparison to the time that the reservoir replacement takes place. If the reservoir remains empty for an extended period, it may be indicative of lengthy shipping times and the controller may update the reorder lead time accordingly. Similarly, if the controller notes an extended empty reservoir period, but notes an associated above-average usage after the reorder command is issued, the controller may decide that the delay is not associated with a shipping delay and rather, is due to an anomalous usage period.

In at least one embodiment, the controller receives input from the automatic monitoring system 90. More specifically, the controller 150 receives input from the proximity sensor 300. The proximity sensor is an always-on device that uses infrared or other technology to determine the presence of a user's hand entering a detection zone under the faucet. Once triggered, the proximity sensor 300 sends a signal to the controller 150, waking the controller if it is in an optional sleep mode, and causing the controller to initiate the washing sequence described below.

The controller, in at least one embodiment, is connected to a camera or scanner 310. The camera 310 is used, as described above, for feedback and/or determination of handwashing completion.

Input From User In many embodiments placing the hands under the faucet to trigger the wash sequence will be the only input from the user. In other embodiments, input from the user may also include gathering information to customize or log the washing sequence, or to cancel or repeat the washing sequence as needed. Such input could include, but is not limited to: sensing a badge or other identifying device that includes a visual barcode, an RFID or Bluetooth tag, a scannable code, or a magnetic signature; facial, fingerprint or voice identification; touch or speak to select language or wash sequence.

Distributed Elements It is preferrable that as much of the functionality as practical be integrated into the faucet housing for reasons including, but not limited to: reducing production costs; reducing the costs, added complexity and failure potential of connections; or support the simple replacement of a single part in case of malfunction. In some embodiments it may be beneficial to locate functions remote from the faucet body: The camera might be beneficially mounted above the faucet to prevent splashing on the lens and provide better viewing; an IR presence sensor might also be susceptible to fouling by splashed cleaning solution and soil from the hands; the radio reception of an RFID ID reader might be better outside the metal faucet housing; and a server or cloud-based control or logging hardware would by definition be located outside the faucet.

Instructions Forms that the instructions can take can vary with the embodiment and include, but are not limited to: verbal or non-verbal instruction by an authority, co-worker or co-user; written instructions and/or language-neutral pictograms provided to the user or posted; written instructions and/or language-neutral pictograms where steps are cued by a visual display visible to the user at the faucet or audio cue audible to the user at the faucet; dynamic written instructions and/or language-neutral pictograms displayed on or near the faucet; audio instructions audible to the user at the faucet; language-specific instruction can be tailored to the preferred language of the user; the preferred language can be preset, determined from a user's identification credentials (E.g., ID badge), or selected by the user (E.g., from a touch screen.)

Communication Modality

In some embodiments the controller 150 is connected to a communication modality 170. The communication modality preferably allows data flow from the controller 150 to a central server, cloud-based server, or other internet or network connection. The communication modality 170 may be in the form of a wi-fi connection, cellular data connection, ethernet connection, Bluetooth connection, or other data links as are known in the present or future arts.

The communications data being transferred may include, but is not limited to, compliance data, feedback, supply data, automatic ordering services, software or firmware updates, maintenance data, user identification data, and the like.

Power Supply

Power is supplied to the handwashing apparatus 20 via a power supply 130. The power supply 130 may be a standard outlet or hardwire connection to a typical 110V or 220V power supply with or without power conditioning such as stepping the power source down to 24 VDC. Alternatively, if the apparatus is to be used as a standalone device, the power supply 130 may be embodied as a rechargeable or disposable battery. Rechargeable batteries may be recharged manually, or through the use of solar power or in-line turbine power placed in the water line.

Handwashing Sequence

Figure 7:
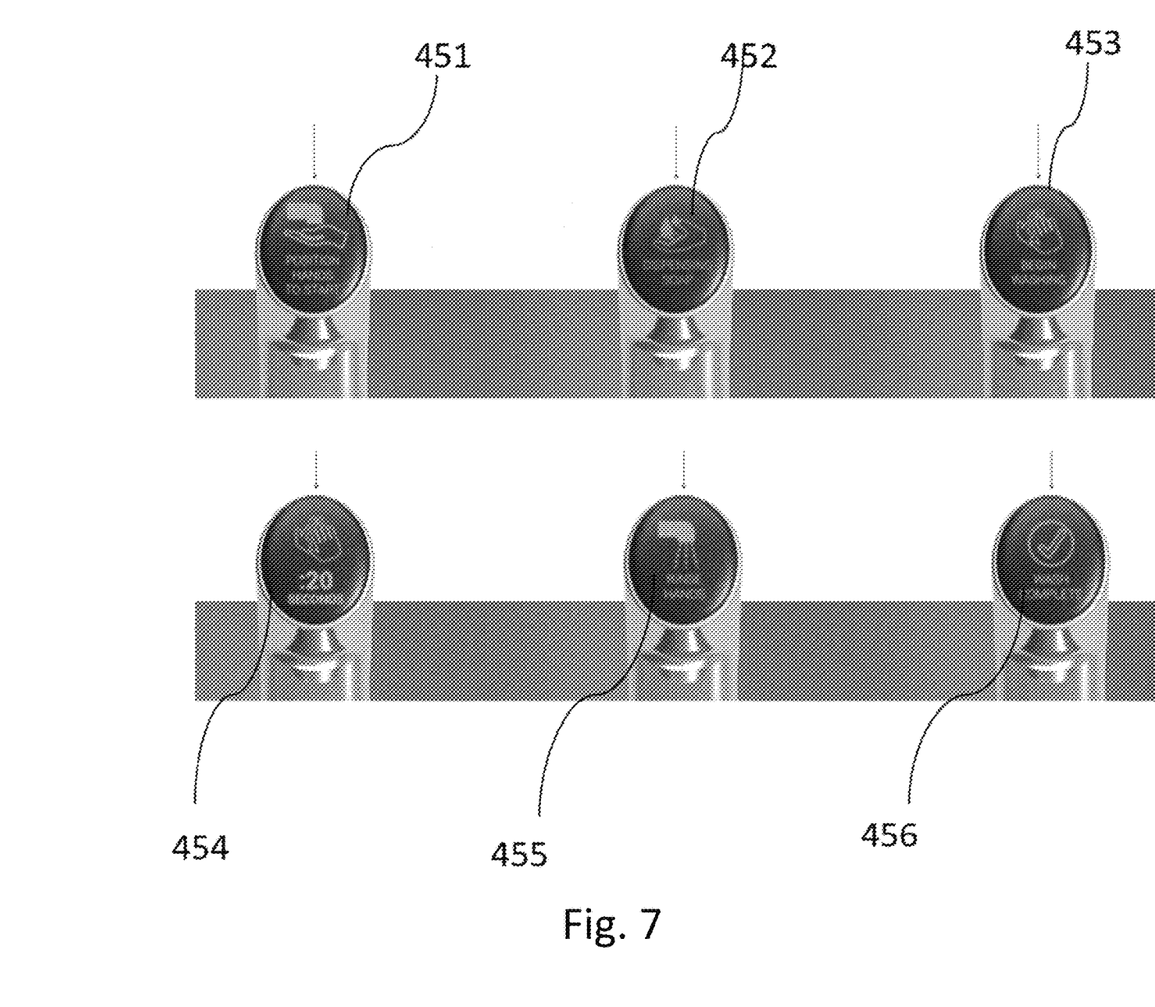
FIG. 7 is a sequence showing an embodiment of a method of the invention and the corresponding messages displayed on the user interface.

Having described the various components and embodiments of the handwashing apparatus 20, attention is now directed to the various messages displayed on the user interface shown in FIG. 7.

The sequence begins at 451, which is automatically activated when a user places their hands under the faucet, activating the sensor 90, which sends a signal to the controller 150 to begin the sequence. The user interface 110 activates, in response to a command from the controller 150, and displays a first message, such as "Position Hands to Start" as shown. Alternatively, universal pictograms or other local languages are shown.

In an alternative embodiment, the message 451 is always displayed between uses, indicating the apparatus 20 is powered on and functional, in which case activating the sensor 90 would signal the controller 150 to activate the next step 452.

In either embodiment, the scanner 90 may register a user identifier, as described above. Details of the handwashing event may then be recorded, either optically with a camera 310 in the form of video footage, non-optical data collection such as for compliance purposes, or both.

The next step 452 displays a message instructing the user to keep their hands under the faucet while the apparatus 20 dispenses water and cleansing agent. The controller 150 sends a signal to the user interface 110 to display this message, while also sending a signal to supply power to the normally-closed solenoid valve 210 causing the solenoid valve 210 to open, thereby dispensing water. The controller 150 also starts a clock such that the supply of power to the solenoid valve is limited to a predetermined desired time interval. After the water is dispensed, the controller 150 sends a signal to the pump 216 to dispense a metered amount of sanitizing solution 50. The controller further logs the sanitizer dispensing event for purposes of tracking cleansing agent usage as described above.

Once the metered amount of sanitizer has been dispensed, the next step 453 is a handwashing assistance step and involves the controller 150 sending a signal to the user interface 110 to display instructions to spread the cleansing agent and scrub the hands together, or the like. The controller 150 also activates the visualization activating mechanism 70 such that interaction commences between the apparatus 20 and the visualization component of the sanitizer solution 50.

In some embodiments, a timer is started at 454 by the controller that counts up or down to ensure a minimum elapsed time passes before moving on to the next step 455. The controller may further send instructions to the user interface 110 to display the value of the timer so the user knows how long is left in the scrubbing step.

In other embodiments, at 454 the camera sends video data to the controller 150 which then initiates an analysis algorithm for determining a percentage of the hand surface of the user is covered with sanitizer solution before moving to the next step. The user interface 110 may show coverage progress in the form of a percentage, or a scale of 1-10, or a simple diagram including a visual indicator of the progress made. In this way, the user is motivated to continue scrubbing until the interface 110 indicates the hands are sufficiently covered. This embodiment may add the desired result of improving the efficiency of the user, who will naturally be motivated to accomplish the task in a minimal amount of time. In some embodiments the count-down timer does not start until the hands are sufficiently covered with sanitizing solution.

The next step 455 occurs when the criteria of step 454 has been satisfied. At 455, the controller 150 signals the user interface 110 to display an indication that scrubbing is complete and that a rinse step is about to commence. The controller further sends a signal to provide power to the solenoid 210 to open the valve and provide a stream of water to rinse the sanitizer solution 50 off the hands.

In some embodiments, the controller further instructs the in-line heater (not shown), preferably at an earlier step, to energize and begin heating the temperature up to a desired temperature. As explained above, the desired temperature may be a user-specific setting associated with the aforementioned user-identification feature, or may be a preset temperature set by an authorized technician or a factory-set temperature.

In some embodiments the user interface 110 further instructs the user how to increase the rinse sequence, perhaps overriding the system completely. For example, if the user is collecting water for a purpose other than cleaning the hands, an override option, perhaps in the form of a button, could be depressed that sends power to the solenoid 210, with or without the involvement of the controller 150.

In some embodiments, the rinse step continues as long as the sensor detects hands under the faucet.

After the rinsing step is complete, the controller 150 sends a signal to stop the flow of power to the solenoid valve 210. The controller 150 sends a signal to the user interface 110 to display a message 456 indicating the handwashing sequence is complete. At this point, or any other point or points in the sequence, data may be transmitted to a cloud-based or other server, internet, or other network.

Configurability

In some embodiments the wash sequence can be configured by a super user with the authority to change most of the presets of the wash sequence including, but not limited to: the pre-rinse time and temperature; the volume of cleansing agent dispensed; the required coverage of the scrubbing step; the duration of the scrubbing step; the duration and temperature of the rinse step; the data to be retained; and the location of the stored data. The super user can assign varying wash configurations to different users. For example, a more rigorous wash for those handling food compared to those working in an office. A super user can grant individual users permission to configure a subset of these presets according to their personal preference.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of washing hands comprising: providing a handwashing apparatus including a sequence and a user interface; providing an activation mechanism for activating the handwashing sequence; providing instruction via the user interface to keep the hands in engagement with the handwashing apparatus until at least a sanitizing solution is dispensed; changing an optical property of the sanitizing solution by activating an energy source onto the sanitizing solution present on the hands; instructing the user to ensure that all surfaces of the hands are covered with the sanitizing solution; using a sensing mechanism connected to the handwashing apparatus to automatically determine whether the surfaces of the hands are sufficiently covered with the sanitizing solution; dispensing water once the sensing mechanism has automatically determined that the surfaces of the hands are sufficiently covered with the sanitizing solution, thereby allowing the user to rinse the surfaces of the hands, and does not dispense water when the sensing mechanism has automatically determined that the surfaces of the hands are not sufficiently cover with the sanitizing solution.

2. The method of claim 1 further comprising recording usage data associated with the handwashing event.

3. The method of claim 2 further comprising using said usage data to determine an amount of sanitizing solution remaining.

4. The method of claim 1 wherein providing instruction via the user interface comprises providing visual and/or audio instruction via the user interface.

5. The method of claim 1 wherein activating an energy source comprises activating a UV light.

6. The method of claim 1 wherein dispensing water once the sensing mechanism has automatically determined that the surfaces of the hands are sufficiently covered with the sanitizing solution further comprises dispensing water after a predetermined time interval has elapsed.

7. The method of claim 1 wherein the sensing system comprises a camera.

8. A handwashing apparatus comprising:
 a dispensing apparatus that uses a sensor to determine the presence of a user's hands;
 a supply of water dispensable by the handwashing apparatus;
 a supply of sanitizing solution;
 a controller associated with the handwashing apparatus that executes the handwashing sequence upon receiving a signal from the sensor or start button;
 wherein the sequence includes:
  a sanitizing solution dispensing step;
  a handwashing assistance step; and,
  a rinsing step;
 wherein the handwashing assistance step includes providing visualization assistance to the user that helps the user determine thorough coverage of the hands with the sanitizing solution;
 wherein the rinsing step is not activated until an automatic sensor determines that thorough coverage of the hands with the sanitizing solution has been accomplished.

9. The handwashing apparatus of claim 8 wherein the automatic sensor determining that thorough coverage of the hands with the sanitizing solution starts a timer that has to expire before the rising step is activated.

10. The handwashing apparatus of claim 8 wherein the automatic sensor performs an optical analysis of a handwashing effort by the user.

11. The handwashing apparatus of claim 8 further comprising a user interface that provides information to the user.

12. The handwashing apparatus of claim 11 wherein the information pertains to which step the user is currently performing.

13. The handwashing apparatus of claim 11 wherein the information provides instructions to the user as to how to complete the step being performed.

* * * * *